(12) United States Patent
Otani et al.

(10) Patent No.: US 8,741,969 B2
(45) Date of Patent: Jun. 3, 2014

(54) ANTI-ADHESION MEMBRANE

(75) Inventors: Hitoshi Otani, Ayabe (JP); Shojiro Matsuda, Ayabe (JP); Tsuguyoshi Taira, Ayabe (JP); Noriyuki Morikawa, Ayabe (JP)

(73) Assignee: Gunze Limited, Kyoto (JP)

( * ) Notice: Subject to any disclaimer, the term of this patent is extended or adjusted under 35 U.S.C. 154(b) by 1078 days.

(21) Appl. No.: 11/989,701

(22) PCT Filed: Aug. 2, 2006

(86) PCT No.: PCT/JP2006/315306
§ 371 (c)(1),
(2), (4) Date: Mar. 25, 2008

(87) PCT Pub. No.: WO2007/018093
PCT Pub. Date: Feb. 15, 2007

(65) Prior Publication Data
US 2009/0099268 A1    Apr. 16, 2009

(30) Foreign Application Priority Data

Aug. 5, 2005  (JP) ................. 2005-228641

(51) Int. Cl.
*A61K 47/42*   (2006.01)
*C07K 1/00*    (2006.01)
*C07K 14/78*   (2006.01)
*A61P 19/04*   (2006.01)

(52) U.S. Cl.
CPC ............. *A61K 47/42* (2013.01); *C07K 14/78* (2013.01); *C07K 1/00* (2013.01)
USPC ..................................... 514/774

(58) Field of Classification Search
None
See application file for complete search history.

(56) References Cited

U.S. PATENT DOCUMENTS

| 6,153,292 A * | 11/2000 | Bell et al. ................. 428/305.5 |
| 2004/0137179 A1 * | 7/2004 | Matsuda et al. ............. 428/36.1 |

(Continued)

FOREIGN PATENT DOCUMENTS

| CA | 2558351 A1 * | 8/2006 |
| JP | 10-113384 | 5/1998 |

(Continued)

OTHER PUBLICATIONS

K. Tomihata, K. Burczak, K. Shiraki, and , Yoshito Ikada; "Cross-Linking and Biodegradation of Native and Denatured Collagen" in Polymers of Biological and Biomedical Significance, Nov. 30, 1993; Chapter 24, pp. 275-286.*

(Continued)

*Primary Examiner* — Ernst V Arnold
(74) *Attorney, Agent, or Firm* — Hamre, Schumann, Mueller & Larson, P.C.

(57) ABSTRACT

An object of the present invention is to provide an anti-adhesion membrane that has no toxicity to a living body, has flexibility allowing itself to fit an affected part as a hydrated gel, is uniformly crosslinked, and is immediately absorbed in a living body after maintaining its shape in the living body for a certain period of time.

The present invention provides anti-adhesion material, which comprises a thermally crosslinked gelatin film, and has a water content of 60 to 85% calculated by the following formula (1):

water content (%)=[$(Ws-Wd)/Ws$]×100(%)    (1), in the formula (1), Ws representing a weight (wet weight) of the anti-adhesion material immersed in a phosphate buffered saline solution at a temperature of 25° C. for one hour, and Wd representing a weight (dry weight) of the anti-adhesion material dried completely using a vacuum drying apparatus.

9 Claims, 1 Drawing Sheet

(56) References Cited

U.S. PATENT DOCUMENTS

| | | |
|---|---|---|
| 2005/0147661 A1 | 7/2005 | Tabata et al. |
| 2006/0094318 A1 | 5/2006 | Matsuda et al. |

FOREIGN PATENT DOCUMENTS

| | | |
|---|---|---|
| JP | 10-265590 | 10/1998 |
| JP | 11-47258 | 2/1999 |
| JP | 11-279296 | 10/1999 |
| JP | 2000-212286 | 8/2000 |
| JP | 2001-510358 | 7/2001 |
| JP | 3517358 | 1/2004 |
| JP | 2004-65780 | 3/2004 |
| JP | 2004-117831 | 4/2004 |
| JP | 2004-209228 | 7/2004 |
| LI | 2003-62063 | 3/2003 |
| WO | 98/22154 | 5/1998 |
| WO | WO 2005111121 A2 * | 11/2005 |

OTHER PUBLICATIONS

Yannas et al. "Cross-linking of Gelatine by Dehydration" Nature, 1967, vol. 215(5100), pp. 509-510.*

Lee, et al., "Regeneration of serous membrane on gelatin-processed polyglycolic acid (PGA)-human collagen membrane and its efficacy on the prevention of adhesion", Journal of Biomedical Materials Research, vol. 64A, No. 1, Dec. 13, 2002, pp. 88-92.

* cited by examiner

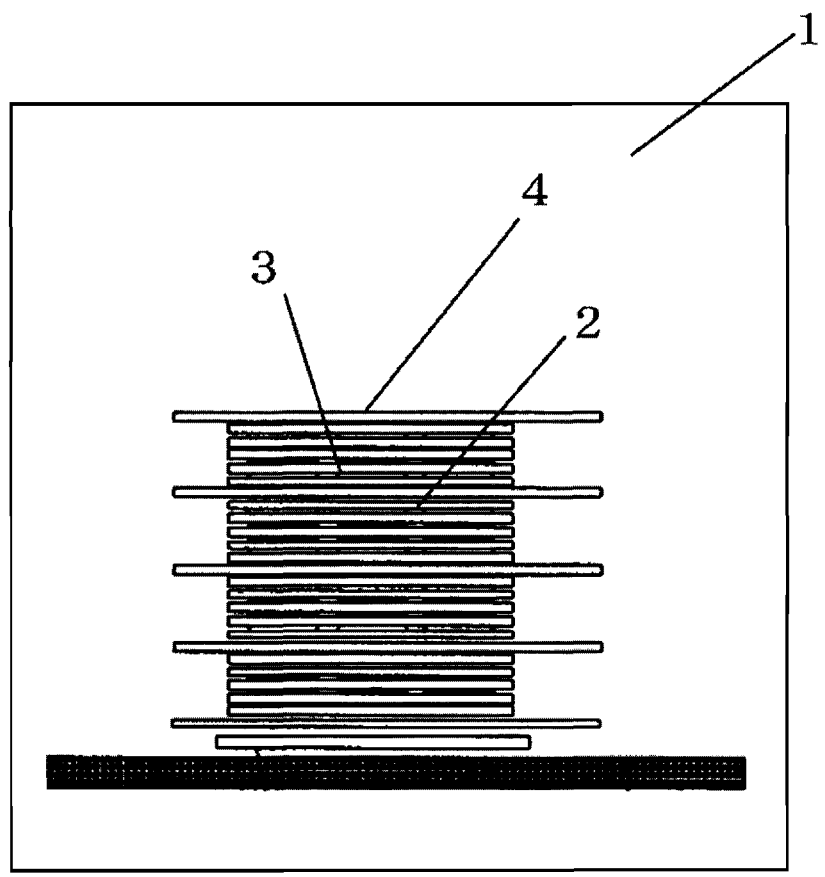

ANTI-ADHESION MEMBRANE

TECHNICAL FIELD

The present invention relates to an anti-adhesion membrane that has no toxicity to a living body, has flexibility allowing itself to fit an affected part as a hydrated gel, is uniformly crosslinked, and is immediately absorbed in a living body after maintaining its shape in the living body for a certain period of time.

BACKGROUND ART

After a surgical operation, living body tissues often adhere to one another to cause a pain or a functional disorder. Adhesion occurs as a serious problem especially in a field such as obstetrics and gynecology, digestive surgery, orthopedics, and cardiovascular surgery, and a severe case requires an operation to separate the adhesion. In addition, occurrence of an adhesion increases risk upon a re-operation of a primary disease. As a method for preventing the adhesion of living body tissues, there has been proposed a method for isolating an area with a possibility of occurrence of the adhesion using a membrane called an anti-adhesion material.

The anti-adhesion material is required to have properties as follows: having flexibility that allows itself to fit an affected part as a hydrated gel; being immediately absorbed by a living body after maintaining its shape in the living body for a certain period of time; causing only slight tissue reaction; and the like. As an anti-adhesion material satisfying the above-mentioned properties, there has been proposed an anti-adhesion material comprising a film containing gelatin (for example, Patent Documents 1 to 6). Gelatin is a polymer derived from a living body, and has an excellent biocompatibility and the like.

However, gelatin films, as they are, absorb water in a living body so as to swell greatly, or are degraded in a very short period of time so as to be deformed. For these reasons, there have been problems that the gelatin films are difficult to handle and fail to produce sufficient effects on prevention of adhesion. In order to solve the problems, Patent Documents 1 to 6 disclose that crosslinking of a film containing gelatin by a suitable method allows the film to have a suitable water-containing property and suitable degradation. For example, Patent Documents 1, 4, 5, and 6 disclose ultraviolet-crosslinking, and Patent Documents 2 and 3 disclose a chemical crosslinking agent used in a combination.

However, there has been a problem that an anti-adhesion material comprising an ultraviolet-crosslinked gelatin film may be deformed in a living body at an early stage of use, in spite of its high degree of crosslinking.

On the other hand, the method of using a chemical crosslinking agent has a problem of a residue of a crosslinking agent or generation of a by-product derived from the crosslinking agent upon degradation in a living body.

Patent Document 1: Japanese Kokai Publication No. Hei-11-47258
Patent Document 2: Japanese Kokai Publication No. Hei-11-279296
Patent Document 3: Japanese Kokai Publication No. 2000-212286
Patent Document 4: Japanese Kokai Publication No. 2003-62063
Patent Document 5: Japanese Kokai Publication No. 2004-209228
Patent Document 6: Japanese Patent No. 3517358

DISCLOSURE OF THE INVENTION

Problem to be Solved by the Invention

The present inventors found out that nonuniform crosslinking formed in an anti-adhesion material comprising an ultraviolet-crosslinked gelatin film causes early deformation of the anti-adhesion material in a living body, in spite of its high degree of crosslinking. That is, in case of obtaining a crosslinked gelatin film by irradiation with ultraviolet rays, the gelatin absorbs the ultraviolet rays, resulting in a higher degree of crosslinking in a part relatively closer to the surface of the gelatin film but a lower degree of crosslinking in a part deep in the thickness direction. Especially, in case of using gelatin containing impurities, irradiating the impurities with ultraviolet rays causes deterioration and discolor in a part of gelatin, leading to absorption of more ultraviolet rays. In case of disposing, in a living body, an anti-adhesion material comprising the above-mentioned gelatin film crosslinked nonuniformly in the thickness direction, although stable appearance of its shape immediately after an operation, degradation of a part neighboring a central part with a low degree of crosslinking proceeds rapidly, and subsequently the central part disappears, resulting in failure to maintain its shape. In addition, the anti-adhesion material comprising the gelatin film nonuniformly crosslinked causes a problem of an inferior property such as poor tensile strength to that of an anti-adhesion material comprising a gelatin film uniformly crosslinked as a whole.

Moreover, the method for using a chemical crosslinking agent causes problems of a residue of the crosslinking agent and release of a substance having a low molecular weight due to degradation of a crosslinked part.

In light of the above-mentioned problems, an object of the present invention is to provide an anti-adhesion membrane that has no toxicity to a living body, has flexibility allowing itself to fit an affected part as a hydrated gel, is uniformly crosslinked, and is immediately absorbed in a living body after maintaining its shape in the living body for a certain period of time.

Means for Solving the Problem

The present invention provides an anti-adhesion material, which comprises a thermally crosslinked gelatin film, and has a water content of 60 to 85% calculated by the following formula (1):

$$\text{water content (\%)} = [(Ws - Wd)/Ws] \times 100 (\%) \quad (1),$$

in the formula (1), Ws representing a weight (wet weight) of the anti-adhesion material immersed in a phosphate buffered saline solution at a temperature of 25° C. for one hour, and Wd representing a weight (dry weight) of the anti-adhesion material dried completely using a vacuum drying apparatus.

Hereinafter, the present invention will be described in detail.

The present inventors has conducted further studies and completed the present invention with the following findings. That is, a thermally crosslinked gelatin film is more uniformly crosslinked than an ultraviolet-crosslinked gelatin film, and also produces no highly toxic substance having a low molecular weight, unlike the case of a method using a chemical crosslinking agent. Patent Documents 6 and the like contain reference of thermal crosslinking of gelatin but no detailed description of a degree of crosslinking or a method for crosslinking required to obtain sufficient performance as an anti-adhesion material.

The anti-adhesion material of the present invention comprises a thermally crosslinked gelatin film.

A material for the gelatin film is not particularly limited, and examples thereof include a gelatin derived from a bone, a tendon, skin and the like from bovine, swine, chicken, salmon and the like.

The preferable lower limit of a weight-average molecular weight, measured by GPC, of gelatin to be used as the material for the gelatin film is 100,000, and the preferable upper limit thereof is 300,000. Gelatin having a weight-average molecular weight of less than 100,000 causes a lowered tensile strength of the obtained anti-adhesion material of the present invention. On the other hand, the upper limit thereof is defined as 300,000, based on a property of gelatin that never has a weight-average molecular weight of more than 300,000. Here, the more preferable lower limit is 150,000 and the more preferable upper limit is 300,000.

The preferable lower limit of a jelly strength of the gelatin to be used as the material for the gelatin film is 150 g, and the preferable upper limit thereof is 350 g. The reason can be explained as follows. Gelatin having a jelly strength of less than 150 g possibly results in the anti-adhesion material of the present invention having a larger deformation ratio or a lower tensile strength. In addition, production of gelatin having a jelly strength of more than 350 g is attended with difficulties. The more preferable lower limit is 250 g, and the more preferable upper limit is 350 g.

Here, in this description, the jelly strength refers to a jelly strength defined in JIS K 6503-2001, and is measured by load required for a 4 mm depression of the surface of a jelly by a plunger having a diameter of 12.7 mm at a speed of 1 mm/s, the jelly being prepared by cooling a 6.67% by weight gelatin solution for 17 hours at a temperature of 10° C.

As the gelatin to be used as a material of the gelatin film, alkali treated gelatin is preferably used due to the significantly low endotoxin content and the excellent safety, and specific examples thereof include alkali treated gelatin derived from cattle and alkali treated gelatin derived from swine produced by Nippi, Incorporated, and the like.

Into the gelatin to be used as a material of the gelatin film, for example, glycerin, polyethylene glycol, hyaluronic acid and the like may be added in an amount not inhibiting the purpose of the present invention, in order to allow the film to have flexibility. In addition, a conventionally well-known additive such as an antimicrobial agent and an anti-inflammatory agent may be added.

The gelatin film can be obtained as follows: a gelatin solution is prepared by dissolving the raw gelatin in a suitable solvent, casted onto a water-repellent glass plate or a water-repellent release sheet such as a sheet (tray) made of polystyrene and a sheet (tray) made of fluorine resin, and then dried.

That is, first, the raw gelatin is dissolved in a solvent under heating. As the above-mentioned solvent, for example, distilled water, dimethyl sulfoxide (DMSO) and the like, or a mixed solution thereof may be used. Out of these, distilled water is preferably used in terms of easy handling.

Although an amount of the gelatin to be added is not particularly limited, the preferable lower limit thereof is 0.1 g with respect to 100 mL of the solvent, and the preferable upper limit thereof is 50 g. Addition of less than 0.1 g of the gelatin may cause difficulties in forming thereof into a film. Addition of more then 50 g of the gelatin may cause difficulties in uniform casting thereof due to the high viscosity. The more preferable lower limit is 1 g, and the more preferable upper limit is 30 g.

Although a temperature for dissolving the gelatin is not particularly limited, the preferable lower limit thereof is 30° C., and the preferable upper limit thereof is 70° C. Dissolution of the gelatin at a temperature of less than 30° C. may require a longer time. Dissolution of the gelatin at a temperature of more than 70° C. may cause degradation and a lowering in molecular weight of the gelatin, leading to a decrease in the jelly strength. The more preferable lower limit is 40° C., and the more preferable upper limit is 60° C.

A non-crosslinked gelatin film can be produced by casting the obtained solution containing the dissolved gelatin into a petri dish made of polystyrene or fluorine resin, and the like, and drying the solution.

A method employed for the above-mentioned drying process is not particularly limited, and for example, air drying, drying by heating, drying under a reduced pressure (vacuum drying), forced exhaust drying, forced circulating convection and the like may be used.

The preferable lower limit of a temperature employed in the above-mentioned drying process is −40° C., and the preferable upper limit thereof is 60° C. Drying of the gelatin film at a temperature of less than −40° C. may require an excessively long time. Drying of the gelatin film at a temperature of more than 60° C. causes degradation and a lowering in molecular weight of the gelatin. The more preferable lower limit is 0° C., and the more preferable upper limit is 40° C.

The above-mentioned series of the production processes of the gelatin film are preferably carried out under aseptic conditions, for example, in a clean bench or a clean room. This is because the gelatin film should be prevented from occurring contamination of bacterial proliferation during operation. For this reason, a production apparatus to be used is preferably sterilized, for example, by an autoclave, EOG (ethylene oxide gas), dry heat, electron rays and the like. Moreover, the gelatin solution is also preferably sterilized, for example, by a conventionally well-known filter filtration sterilization, before used in the above-mentioned processes.

The gelatin film obtained as described above is thermal-crosslinked.

Thermal crosslinking allows the gelatin film to be more uniformly crosslinked than ultraviolet-crosslinking, and also produces no highly toxic substance having a low molecular weight, unlike the case of a method using a chemical crosslinking agent.

Although a method employed for the above-mentioned thermal crosslinking process is not particularly limited, the film is preferably heated uniformly from the both faces thereof. Heating from the both faces enables the gelatin film to have a shape uniformly crosslinked even in the thickness direction.

Heating is preferably carried out under a reduced pressure of 1 Torr or less. The reduced pressure enables suppression of thermal decomposition of the gelatin caused by heating.

As a method employed for the above-mentioned thermal crosslinking process of the gelatin film, the preferable method is that the non-crosslinked gelatin film sandwiched between two sheets having the same thermal conductivity is heated under a reduced pressure. A method of this kind allows heat to be uniformly conducted to the non-crosslinked gelatin film through the two sheets, resulting in a uniform crosslinked shape of the gelatin film in both of the thickness direction and the plane direction.

The method for producing an anti-adhesion material which comprises a step of thermal-crosslinking including heating under a reduced pressure with a non-crosslinked gelatin film sandwiched between two sheets having the same thermal conductivity is also one aspect of the present invention.

Here, in case of carrying out thermal crosslinking simultaneously on a large number of non-crosslinked gelatin films, the gelatin films and the sheets having the same thermal conductivity needs to be laminated alternately to form a shape in which each of the gelatin film is sandwiched between the above-mentioned two sheets. However, a large number of laminated sheets may cause nonuniform heat distribution between a peripheral part and a central part of a laminated part. That is, thermal conduction may vary according to a distance from a heat source. In this case, insertion of materials having an excellent thermal conductivity such as an aluminum plate at a suitable interval allows uniform thermal conduction, resulting in prevention of nonuniformity of crosslinking in lot. Accordingly, a more uniformly thermally crosslinking can be carried out by carrying out thermal-crosslinking treatment with control of thermal conductivity using a combination of sheets each having a different thermal conductivity.

The figure shows a schematic view of a preferable embodiment in which thermal crosslinking is simultaneously carried out on a large number non-crosslinked gelatin films. In the figure, in a vacuum dryer 1, non-crosslinked gelatin films 2 and fluorine resin sheets 3 are alternately laminated in such a manner that the gelatin film 2 is sandwiched between the two fluorine resin sheets 3. Moreover, an aluminum plate 4 is disposed on every five sheets of the fluorine resin sheets 3 to allow heat to be uniformly conducted as a whole.

The method for producing an anti-adhesion material, which comprises a step of carrying out thermal-crosslinking treatment with control of thermal conductivity using a combination of sheets each having a different thermal conductivity, is also one aspect of the present invention.

Furthermore, insertion of a sheet-shaped heat source is also one aspect of the present invention. The above-mentioned method allows more uniform thermal crosslinking.

As the sheet-shaped heat source, examples thereof include a silicone rubber heater comprising a combination of a temperature controller and glass fiber reinforced silicone rubber sheets holding therebetween an electric heating nickel chrome, a silicone sheet heater, a metal heater and the like.

Use of these sheet-shaped heat sources as they are, uses of them alternately laminated with the above-mentioned aluminum plates, or use of the sheet-shaped heat source sandwiched between the aluminum plates allows the whole face of the gelatin film to be heated more uniformly.

The above-mentioned thermal crosslinking process is carried out to obtain the water content calculated by the following formula (1) of 60 to 85%. The water content can be used as an indicator reflecting a degree of crosslinking, and a low water content indicates a high degree of crosslinking.

$$\text{Water content (\%)} = [(Ws - Wd)/Ws] \times 100(\%) \qquad (1)$$

In the formula (1), Ws representing a weight (wet weight) of the anti-adhesion material immersed in a phosphate buffered saline solution at a temperature of 25° C. for one hour, and Wd representing a weight (dry weight) of the anti-adhesion material dried completely using a vacuum drying apparatus.

The anti-adhesion material having a water content of less than 60% has the rubber-like elasticity and an excellent shape retention property, but is slowly degraded upon disposed in a living body, possibly resulting in lowered performance for prevention of an adhesion. The anti-adhesion material having a water content of more than 85% has a lowered shape retention property, and is quickly degraded upon disposed in a living body, resulting in loss of the shape at an early stage. The preferable lower limit is 65%, and the preferable upper limit is 80%.

In order to obtain an anti-adhesion material having the water content within this range, conditions for thermal crosslinking are preferably suitably set approximately as follows: under a reduced pressure (1 Torr); at a temperature of 120 to 170° C.; and for 30 minutes to 72 hours.

Generally, heat treatment at a high temperature and heat treatment for a longer time produce a lot of crosslinking shapes leading to a high degree of crosslinking. A high degree of crosslinking indicates a low water content.

Therefore, in order to obtain desired quality, conditions are suitably set to carry out thermal crosslinking. Thermal crosslinking at a lower temperature requires a longer time for crosslinking. On the other hand, thermal crosslinking at a higher temperature tends to cause a fragility of the film, thus leading to increased possibility of fracture in the film.

One example of the more preferable conditions for thermal crosslinking to obtain the anti-adhesion material of the present invention is given as follows: at a temperature of 120 to 150° C.; and for 5 to 30 hours.

The preferable lower limit of a tensile strength of the anti-adhesion membrane of the present invention is 1 N, measured by a method according to JIS L 1912-1997 after immersion of a sample having a width of 1 cm in a phosphate buffered saline solution at a temperature of 25° C. for one hour. Practically, an anti-adhesion membrane having a tensile strength of less than 1 N possibly causes difficulties in use. Although the upper limit is not particularly limited, it is difficult to obtain an anti-adhesion membrane having a tensile strength of more than 10 N. Although a higher degree of crosslinking leads to a higher strength, an excessively high degree of crosslinking leads to fragility, resulting in lowering in a degree of elongation and strength. Moreover, since a lower degree of crosslinking leads to a lower strength, before sufficiently being elongated, fracture takes place in an anti-adhesion membrane.

In the anti-adhesion membrane of the present invention, the preferable lower limit of a deformation ratio calculated by the following formula (2) is 95%, and the preferable upper limit thereof is 120%. The deformation ratio can be used as an indicator reflecting operationality in use. A deformation ratio deviating more distantly from 100% indicates more negative handling.

$$\text{Deformation ratio (\%)} = (Ss/Sd) \times 100(\%) \qquad (2)$$

In the formula (2), Ss representing an area of the anti-adhesion material immersed in the phosphate buffered saline solution at a temperature of 25° C. for one hour, and Sd representing an area of the anti-adhesion material before the immersion. An anti-adhesion material having the deformation ratio of less than 95% fails to maintain an area required to cover an affected part. An anti-adhesion material having the deformation ratio of more than 120% may cause difficulties in operation. (Especially an anti-adhesion material containing a reinforcing material may cause difficulties to handle with such as curling up.) The more preferable lower limit is 100%, and the more preferable upper limit is 110%.

Here, a high degree of crosslinking leads to a low deformation ratio.

The anti-adhesion membrane of the present invention may be further reinforced by a reinforcing material made of a bioabsorbable polymer. Since the reinforcing material made of a bioabsorbable polymer is biodegraded and absorbed in a living body, use of a reinforcing material of this kind for reinforcing the anti-adhesion membrane of the present invention does not need re-operation and the like, and allows the anti-adhesion membrane to have a sufficient strength for preventing itself from damaging due to suture and the like.

Although the bioabsorbable polymer is not particularly limited, polylactic acid, lactic acid-caprolactone copolymer, polyglycolic acid and the like are suitably used, owing to the suitable strength and degradation.

An embodiment of the reinforcing material is not particularly limited, and examples thereof include a nonwoven fabric, a textile fabric, a knitted fabric, a braided rope, a film and the like. In terms of difficulty in being frayed when being fixed by a suture, a long-staple nonwoven fabric, a gause fabric, a warp knitted fabric and the like are suitably used.

Hydrophilization treatment may be carried out on the surface of the reinforcing material. The hydrophilized surface of the reinforcing material is allowed to more firmly contact the gelatin film, resulting in less possibility of detachment of the reinforcing material from the gelatin film. The above-mentioned hydrophilization treatment is not particularly limited, and examples thereof include plasma treatment, glow discharge treatment, corona discharge treatment, ozonization, surface graft treatment, coating treatment, chemical treatment, ultraviolet-rays irradiation treatment and the like.

Although an embodiment of the reinforcement by the reinforcing material is not particularly limited, for example, preferable examples thereof include an embodiment in which the reinforcing material is disposed in the surface and/or the inside of the gelatin film and united together.

Moreover, a part to be reinforced is not particularly limited, the whole gelatin film may be reinforced, or only a part to be sutured and the like may be reinforced.

A method for reinforcing by the reinforcing material is not particularly limited, and examples thereof are given as follows: a method in which the reinforcing material is immersed in the gelatin solution casted into a petri dish and the like, and the obtained reinforcing material containing the gelatin solution inside thereof was dried (first method); a method in which the gelatin solution casted into a perti dish and the like is allowed to gelatinize, and the reinforcing material is placed on the gelatin immediately before completion of the gelatinization and then dried after the completion of the gelatinization (second method); a method in which a complex of the reinforcing material and the gelatin film united together in the second method is immersed in the gelatin solution with the reinforcing material facing the gelatin solution (third method); a method in which two glass plates are preliminarily disposed facing each other to obtain an anti-adhesion membrane having a predetermined thickness, and allowed to hold a reinforcing material having a desired shape therebetween, and then the gelatin solution is casted between the glass plates, and dried after cooled for gelatinization (forth method); and the like.

Effects of the Invention

Since the anti-adhesion material of the present invention comprises a gelatin film that is thermally-crosslinked to have a certain water content, the anti-adhesion material has a uniformly degree of crosslinking as a whole. In addition, compared with an anti-adhesion material comprising an ultraviolet-crosslinked gelatin film, the anti-adhesion material of the present invention has a higher strength, and also a more excellent shape stability in a living body. Furthermore, compared with an anti-adhesion material comprising a gelatin film crosslinked using a chemical crosslinking agent, the anti-adhesion material of the present invention advantageously have no possibility of release of a toxic substance having a low molecular weight.

Particularly, the anti-adhesion material of the present invention is suitably used for preventing an adhesion of pericardium. The anti-adhesion material for a pericardium comprising the anti-adhesion material of the present invention is also one aspect of the present invention.

The present invention provides an anti-adhesion membrane that has no toxicity to a living body, has flexibility allowing itself to fit an affected part as a hydrated gel, is uniformly crosslinked, and is immediately absorbed in a living body after maintaining its shape in the living body for a certain period of time.

BRIEF DESCRIPTION OF DRAWINGS

The FIGURE is a side view of a structure for providing thermal-crosslinking to gelatin films used in an example of the present invention.

BEST MODE FOR CARRYING OUT THE INVENTION

Hereinafter, the present invention will be described in more detail by way of Examples, but the present invention is not limited to these Examples.

Example 1

Gelatin (produced by Nippi, Inc., alkali treated product derived from swine, weight-average molecular weight: 132,000, jelly strength: 257 g) was dissolved in distilled water to obtain a solution containing 5% by weight of the gelatin. An amount of 13 mL of the obtained solution was casted into a petri dish (size: 14 cm×10 cm) made of polystyrene resin, and air dried as it was to obtain a non-crosslinked gelatin film having a thickness of approximately 40 μm.

A laminated body of the non-crosslinked gelatin films having a thickness of 160 μm was obtained by laminating four sheets of the non-crosslinked gelatin films. Each of the non-crosslinked gelatin films forming the laminated body of the non-crosslinked gelatin film was assigned one of numbers 1, 2, 3 and 4 in a sequential order from the top.

Fluorine resin sheets having a thickness of 1 mm were disposed on the both faces of the obtained laminated body of the non-crosslinked gelatin film. In addition, aluminum plates having a thickness of 3 mm were disposed on the both faces of the obtained laminated body, and the resulting laminated body was disposed on a shelf in a vacuum drying apparatus. In this state, thermal crosslinking was carried out under a pressure of 1 Torr or less at a temperature of 135° C. for 8 hours.

Comparative Example 1

A laminated body of non-crosslinked gelatin film obtained by the same method as that of Example 1 was irradiated with ultraviolet rays from a face of a film 1 for 10 hours at a strength of 0.25 mW/cm$^2$ (15 W bactericidal lamp, distance: 50 cm) to carry out ultraviolet-crosslinking.

Comparative Example 2

A laminated body of non-crosslinked gelatin film obtained by the same method as that of Example 1 was irradiated with ultraviolet rays from a face of a film 1 in the same method as that of Comparative Example 1. Subsequently, the laminated body is further irradiated with ultraviolet rays in the same method from a face of a film 4 to carry out ultraviolet ray treatment on the both faces of the laminated body. (each one face: 10 hours, total irradiation: 20 hours)

(Evaluation)

The water content was measured based on the following method for each of four gelatin films forming the laminated body of the gelatin film after crosslinked. That is, each of the gelatin films was dried in a vacuum drying apparatus under a reduced pressure of 1 Torr or less at a temperature of 25° C. for approximately 24 hours to measure the dry weight thereof. On the other hand, each of the gelatin film was immersed in a phosphate buffered saline solution having a temperature of 25° C. for 1 hour to measure the wet weight.

The water content was calculated by the above-mentioned formula (1) using the obtained dry weight and wet weight.

Table 1 shows the results.

TABLE 1

| | Water content (%) | | |
|---|---|---|---|
| | Example 1 | Comparative Example 1 | Comparative Example 2 |
| Film 1 | 67.7 | 74.2 | 72.0 |
| Film 2 | 68.2 | 81.8 | 77.7 |
| Film 3 | 68.2 | 84.4 | 77.6 |
| Film 4 | 67.6 | 87.5 | 73.9 |

Table 1 shows that the four gelatin films thermally crosslinked in Example 1 had almost the same water content. However, in Comparative Example 1 in which ultraviolet-crosslinking is carried out, the film located closer to the face that was not subjected to the direct irradiation with ultraviolet rays had a higher water content (that is, a low degree of crosslinking). Furthermore, in Comparative Example 2 in which ultraviolet-crosslinking is carried out, the films 2 and 3 had a higher water content (that is, a lower degree of crosslinking) than that of the films 1 and 4 that were irradiated with ultraviolet rays. In both Comparative Examples, the obtained films were less uniformly crosslinked than those obtained by thermal crosslinking.

The results show distribution of the water contents every 40 μm in the depth direction of the gelatin films when thermal crosslink was carried out on the non-crosslinked gelatin film having a thickness of approximately 160 μm or ultraviolet-crosslinking was carried out on only one face or the both faces of the non-crosslinked gelatin film having a thickness of approximately 160 μm. That is, thermal crosslinking allows the gelatin film to be more uniformly crosslinked than ultraviolet-crosslinking.

Example 2

Gelatin (produced by Nippi, Inc., alkali treated product derived from swine, weight-average molecular weight: 191, 000, jelly strength: 255 g) was dissolved in distilled water to obtain a solution containing 5% by weight of the gelatin. An amount of 50 mL of the obtained solution was casted into a petri dish (size: 14 cm×10 cm) made of polystyrene resin, and air dried as it was. As a result, 20 sheets of non-crosslinked gelatin films having a thickness of approximately 160 μm were obtained.

The non-crosslinked gelatin films were allowed to leave at rest in a manner shown in the figure in a vacuum drying apparatus. That is, gelatin films and fluorine resin sheets having a thickness of 1 mm were laminated alternately to form a shape in which the non-crosslinked gelatin film is sandwiched between two fluorine resin sheets without failure. Furthermore, an aluminum plate having a thickness of 3 mm was disposed on every five non-crosslinked gelatin films.

Here, each of the non-crosslinked gelatin films was assigned one of numbers of 1, 2, 3 . . . 20 in a sequential order from the bottom.

In this state, thermal crosslinking was carried out under a pressure of 1 Torr or less at a temperature of 135° C. for 8 hours.

(Evaluation)

The water content was measured based on the above-mentioned method for each of four gelatin films 3, 8, 13, 18 selected from the 20 sheets of the crosslinked gelatin films.

Table 2 shows the results.

TABLE 2

| | Water content (%) |
|---|---|
| Film 3 | 69.3 |
| Film 8 | 69.9 |
| Film 13 | 71.4 |
| Film 18 | 71.6 |

Table 2 shows that the obtained films had almost the same water content, irrespective of positions of the films disposed in a vacuum drying apparatus.

Example 3

Gelatin (produced by Nippi, Inc., alkali treated product derived from swine, weight-average molecular weight: 132, 000, jelly strength: 257 g) was dissolved in distilled water to obtain a solution containing 5% by weight of the gelatin. An amount of 50 mL of the obtained solution was casted into a petri dish (size: 14 cm×10 cm) made of polystyrene resin, and air dried as it was to obtain a non-crosslinked gelatin film having a thickness of approximately 160 μm.

Fluorine resin sheets having a thickness of 1 mm were disposed on the both faces of the obtained laminated body of the non-crosslinked gelatin film. In addition, aluminum plates having a thickness of 3 mm were disposed on the both faces of the obtained laminated body, and the resulting laminated body was disposed on a shelf in a vacuum drying apparatus. In this state, thermal crosslinking was carried out under a pressure of 1 Torr or less at a temperature of 135° C. for 8 hours.

COMPARATIVE EXAMPLE 3

A non-crosslinked gelatin film having a thickness of approximately 160 μm was produced by the same method as that of Example 3. The obtained non-crosslinked gelatin film was irradiated with ultraviolet rays for 10 hours on each faces at a strength of 0.25 mW/cm$^2$ (15 W bactericidal lamp, distance: 50 cm) to carry out ultraviolet-crosslinking on the both faces.

(Evaluation)

The evaluation was carried out based on the following method for each of the anti-adhesion materials produced in Example 3 and Comparative Example 3.

Table 3 shows the results.

(1) Measurement of Tensile Strength

The measurement was carried out based on a method according to JIS L 1912-1997. That is, a sample was cut into a size having a width of 1 cm and a length of 3 cm, and immersed in a phosphate buffered saline solution having a temperature of 25° C. for 1 hour. Subsequently, after wiping off excessive water on the surface, the sample was set in a tensile test machine (Instron 4302 produced by Instron, Co., Ltd.) with a distance between clamps of 1 cm, and pulled at a crosshead speed of 100 mm/min to obtain a stress as the tensile strength upon fracture thereof.

(2) Measurement of Deformation Ratio

A sample is cut into a size of a width of approximate 1 cm and a length of approximate 3 cm, and the sides of the sample were accurately measured using a slide caliper to calculate an area Sd. After the sample was immersed in a phosphate buffered saline solution having a temperature of 25° C. for 1 hour, excessive water on the surface is wiped off, and the sides were again measured accurately using a slide caliper to calculate an area Ss.

The deformation ratio was calculated by the above-mentioned formula (2).

(3) Measurement of Water Content

The same method as that of Example 1 was employed for the measurement.

(4) Evaluation of Animal Experiment

Each of the obtained anti-adhesion materials was cut into a size of 1 cm×1.5 cm, and then implanted in an abdominal cavity of a wistar rat (five-week age). The evaluation was carried out based on visual observation of states of the anti-adhesion materials upon incision after a period of 1, 2, 3, 4, 6 and 8 weeks according to the following standard.

◯: Anti-adhesion material maintained its shape till four weeks, and disappeared completely in six weeks.

X: Anti-adhesion material lost its shape and almost disappeared in three weeks.

TABLE 3

|  | Tensile strength (N) | Deformation ratio (%) | Water content (%) | Evaluation of animal experiment |
|---|---|---|---|---|
| Example 3 | 4.52 | 107.8 | 77.4 | ◯ |
| Comparative Example 3 | 2.89 | 109.8 | 76.2 | X |

Industrial Applicability

The present invention provides an anti-adhesion membrane that has no toxicity to a living body, has flexibility allowing itself to fit an affected part as a hydrated gel, is uniformly crosslinked, and is immediately absorbed in a living body after maintaining its shape in the living body for a certain period of time.

BRIEF DESCRIPTION OF THE DRAWINGS

The figure is a schematic view showing a preferable embodiment in which thermal crosslinking is carried out simultaneously on a large number of non-crosslinked gelatin films.

EXPLANATION OF SYMBOLS

| 1 | Vacuum drying apparatus |
| 2 | Non-crosslinked gelatin film |
| 3 | Fluorine resin sheet |
| 4 | Aluminum plate |

The invention claimed is:

1. A method for producing an anti-adhesion material that comprises a thermally crosslinked gelatin film and a water content of 60 to 85% calculated by the following formula (1):

$$\text{water content (\%)} = [(Ws-Wd)/Ws] \times 100(\%) \quad (1),$$

where Ws represents a weight (wet weight) of the anti-adhesion material immersed in a phosphate buffered saline solution at a temperature of 25° C. for one hour, and Wd represents a weight (dry weight) of the anti-adhesion material dried completely using a vacuum drying apparatus, the thermally crosslinked gelatin film including thermal-crosslinks formed under pressure of one Torr or less at a temperature of 120 to 170° C. for 30 minutes to 72 hours, the method comprising:

laminating alternately non-crosslinked gelatin films and fluorine resin sheets so as to form a laminated body having a configuration in which each of the non-crosslinked gelatin films is sandwiched between the fluorine resin sheets, and thermally crosslinking the non-crosslinked gelatin films in the laminated body by heating the laminated body under pressure of one Torr or less at a temperature of 120 to 170° C. for 30 minutes to 72 hours.

2. A method for producing the anti-adhesion material according to claim 1, further comprising inserting within the laminated body or disposing on the surface of the laminated body, a sheet having a thermal conductivity that is higher than a thermal conductivity of each of the fluorine resin sheets.

3. The method of claim 2, wherein the sheet having a thermal conductivity that is higher than a thermal conductivity of each of the fluorine resin sheets is an aluminum plate.

4. The method of claim 2, wherein a plurality of sheets having a thermal conductivity that is higher than a thermal conductivity of the fluorine resin sheets are provided within the laminated body or on the surface of the laminated body.

5. The method for producing the anti-adhesion material according to claim 1, wherein the anti-adhesion material has a tensile strength of 1 to 10 N measured by a method according to JIS L 1912-1997 after immersion of a sample having a width of 1 cm in a phosphate buffered saline solution at a temperature of 25° C. for one hour.

6. The method for producing the anti-adhesion material according to claim 1, wherein the anti-adhesion material has a deformation ratio of 95 to 120% calculated by the following formula (2):

$$\text{deformation ratio (\%)} = (Ss/Sd) \times 100(\%) \quad (2)$$

in the formula (2), Ss representing an area of the anti-adhesion material immersed in the phosphate buffered saline solution at a temperature of 25° C. for one hour, and Sd representing an area of the anti-adhesion material before the immersion.

7. The method for producing the anti-adhesion material according to claim 1, wherein raw gelatin forming the gelatin film has a weight-average molecular weight of 100,000 to 300,000.

8. The method for producing the anti-adhesion material according to claim 1, wherein raw gelatin forming the gelatin film has a jelly strength of 150 to 350 g measured by a method defined in JIS K 6503-2001.

9. The method for producing the anti-adhesion material according to claim 1, further comprising providing a reinforcing material either on the surface of one of the non-crosslinked gelatin films or inside one of the non-crosslinked gelatin films, the reinforcing material comprising a bioabsorbable polymer that reinforces the anti-adhesion material.

* * * * *